(12) United States Patent
Kennefick

(10) Patent No.: US 6,983,226 B2
(45) Date of Patent: Jan. 3, 2006

(54) MICROSTRUCTURE CONTAINING ENTITIES ROTATING UNDER AN APPLIED LOAD TO ENHANCE TOUGHENING AGAINST FRACTURE

(76) Inventor: Christine M. Kennefick, 2029 Turtle Pond Dr., Reston, VA (US) 20191

( * ) Notice: Subject to any disclaimer, the term of this patent is extended or adjusted under 35 U.S.C. 154(b) by 894 days.

(21) Appl. No.: 09/919,922

(22) Filed: Aug. 2, 2001

(65) Prior Publication Data

US 2002/0016686 A1   Feb. 7, 2002

Related U.S. Application Data

(63) Continuation-in-part of application No. 09/164,363, filed on Oct. 1, 1998, which is a continuation-in-part of application No. 08/805,466, filed on Feb. 25, 1997, now Pat. No. 5,826,213.

(51) Int. Cl.
*G06F 17/50* (2006.01)
*G06F 17/10* (2006.01)
*G06G 7/48* (2006.01)

(52) U.S. Cl. .............................................. 703/1; 703/6
(58) Field of Classification Search .................... 703/1, 703/6
See application file for complete search history.

(56) References Cited

U.S. PATENT DOCUMENTS 5,605,584 A * 2/1997 DeLuca et al. ............. 148/410

OTHER PUBLICATIONS

N.I. Muskhelishvili, *Some Basic Problems of the Mathematical Theory of Elasticity*, Fourth Edition, English Translation, P. Noordhoff Ltd., Groningen, The Netherlands, 1963.
T. Hirano and K. Niihara, *Microstructure and Mechanical Properties of $Si_3N_4/SiC$ Composites*, Materials Letters, vol. 22, pp. 249-254 (1995).
Koichi Niihara, *New Design Concept of Structural Ceramics-Ceramics Nanocomposites*, The Centennial Memorial Issue of The Ceramic Society of Japan, vol. 99, No. 10, pp. 974-982 (1991).

* cited by examiner

*Primary Examiner*—Hugh Jones
(74) *Attorney, Agent, or Firm*—Dykema Gossett, PLLC

(57) ABSTRACT

A composite material having a microstructure model is provided with a continuous matrix of microstructure entities such as particles and grains that rotate under both remotely applied stresses and induced concentrated stresses from nearby cracks, pores and smaller particles, all networked within the matrix. The rotation microstructure entities are smooth closed contours that are elliptically-shaped. A net moment results on the boundaries of the microstructure entities effecting fracture toughening of the material. Small particles and other microstructural entities may reduce the attenuation of, transmit, and counteract the stresses induced by the rotating microstructure entities. The induced stresses counteract those stresses and strain energy densities that promote crack propagation. The result is a microstructure free of laminates, coatings, fibers and fiber architectures that effect toughening of the material against fracture.

8 Claims, 2 Drawing Sheets

MICROSTRUCTURE CONTAINING ENTITIES ROTATING UNDER AN APPLIED LOAD TO ENHANCE TOUGHENING AGAINST FRACTURE

RELATED APPLICATION

This application is a continuation-in-part (CIP) application of U.S. application Ser. No. 09/164,363, filed on Oct. 1, 1998, which is a continuation-in-part (CIP) of U.S. application Ser. No. 08/805,466 filed Feb. 25, 1997, now U.S. Pat. No. 5,826,213 issued Oct. 20, 1998.

The present invention was made with Government support from an American Society for Engineering Education Fellowship.

BACKGROUND OF THE INVENTION

1. Field of the Invention

The present invention is directed to a composite material having a microstructure model with properties to improve fracture toughening, and in particular to a microstructure model including entities that rotate under both an applied load and additional induced loads in order to counteract, deflect and prevent crack propagation from moving throughout the material.

2. Discussion of the Related Art

This invention pertains to subject matter disclosed in U.S. Pat. No. 5,826,213, the text of which is hereby incorporated by reference. The present invention uses principles from materials engineering in which to tailor a microstructure of a material to desirable properties or for a specific device. The invention also utilizes principles of applied mechanics in which to prevent crack propagation through a microstructure based upon mechanical interaction with applied loads. Additionally, this invention uses complex variables to determine the interaction of the microstructure with applied loads based upon principles of applied mathematics as disclosed by N. I. Muskhelishvili, *Some Basic Problems of the Mathematical Theory of Elasticity*, Fourth Edition, English Translation, P. Noordhoff Ltd., Groningen, The Netherlands, 1963; N. I. Muskhelishvili, *Praktisiche Lösung der fundamentalen Randwertaufgaben der Elastizitätstheorie in der Ebene für einige Berandungsformen*, Zeitschrift für Angewandte Mathematik und Mechanik, volume 13, pages 264–281 (1933).

Many techniques have been used to enhance material toughening against fracture, including the use of fibers, coatings, laminates, particles and phase transformations in the microstructure of composite materials. Such well-known techniques include composites that contain short cylindrical fibers added to and dispersed within the material, or strips and laminate layers running the entire length of the material used in a device. Other toughened microstructures feature the use of chemical additions and resulting residual stresses of small nanoparticles as disclosed by T. Hirano and K. Niihara, *Microstructure and Mechanical Properties of Si₃N₄/SiC Composites*, Materials Letters, volume 22, pages 249–254 (1995); and Koichi Niihara, *New Design Concept of Structural Ceramics-Ceramics Nanocomposites*, The Centennial Memorial Issue of The Ceramic Society of Japan, volume 99, number 10, pages 974–982 (1991).

The techniques of the prior art rely upon the residual stresses, in microstructures arising either from thermal expansion mismatch during heating and cooling or from phase transformations, to interact with the catastrophic concentrated stresses around a crack tip in order to reduce the chance of crack propagation. Although these residual stresses may be set once fabrication or a phase transformation is completed, they might be attenuated by a large applied load itself before they can negate part of the concentrated stress around a crack tip, thereby making such techniques inefficient. Furthermore, the layup of composites comprising fibers, coating and laminates in lightweight ceramics and intermetallics involves several process steps, thereby increasing the cost of producing the composite.

Another problem with the prior art is that once a crack has passed a particular entity or additive, however, such entity or additive has in most cases lost its ability through unloading to interact with or deflect other cracks. It would be desirable therefore to have a composite material based upon a microstructural model including entities that prevent cracks from moving rather than having the cracks propagate through the material.

SUMMARY OF THE INVENTION

It is an object of the present invention to improve fracture toughening with a composite material having a microstructure model that overcomes the drawbacks of the prior art. In particular, a microstructure model includes entities whose boundaries are smooth closed curves or contours that rotate through a small angle from a mechanical moment on them. The primary source of fracture toughening originates from the mechanical rotation of these entities, whose outer boundaries aside from faceting and irregularities at the atomic level, are elliptically shaped in a preferred embodiment.

The rotational movement gives rise to strain in the surrounding matrix whose associated elastic stresses form alternating regions of compression and tension. The alternating regions of compression and tension can add to existing stresses in such a way as to reduce strain energy promoting fracture. Additionally, the alternating regions of tension and compression can serve as initial conditions for vibrations in the atomic lattice of the material that will absorb energy. The absorption of energy from the vibrations is also expected to reduce the amount of strain energy available for release from the propagation of a crack.

It is another object of the present invention to provide a microstructure whose stresses that are used to prevent fracture actually respond to an applied load and increase as the applied load gets larger. This requires the microstructure to include entities which actually interact with nearby cracks, pores and flaws so as to stop cracks and to counteract associated flaws arising therefrom. A primary objective of the invention is to stop cracks from moving rather than having them deflect around various microstructural entities or additives. Moreover, as an applied load is increased, the angle of rotation increases, with a subsequent increase in the intensity of the induced stresses from strain in the matrix material. The degree of counteraction to built up strain energy from the applied load is therefore expected to increase.

It is a further object of this invention to utilize a relatively simple microstructure entity configuration, which in a preferred embodiment, may include grains and particles that can be patterned primarily through heating and cooling, in addition to making use advantageously of subsequent pores and microcracks that arise naturally. By having a microstructure with the entities being grains or particles set into a matrix material, the present invention avoids the necessary fiber architectures, coatings or phase transformation of the prior art that increase costs of manufacturing and fabrication. The present invention also eliminates the lengthy fabrication processes of the prior art associated with the aforementioned well-known techniques.

With the rotation being the primary source of toughening, the resulting shear stresses due to the rotation near and on a curved boundary are also expected to contribute forces that can add to existing stresses in such a way as to reduce again the strain energy available for release during crack propagation. Other objects and advantages will be apparent from the drawings and specification which follows.

DETAILED DESCRIPTION OF THE INVENTION

Figure 1:
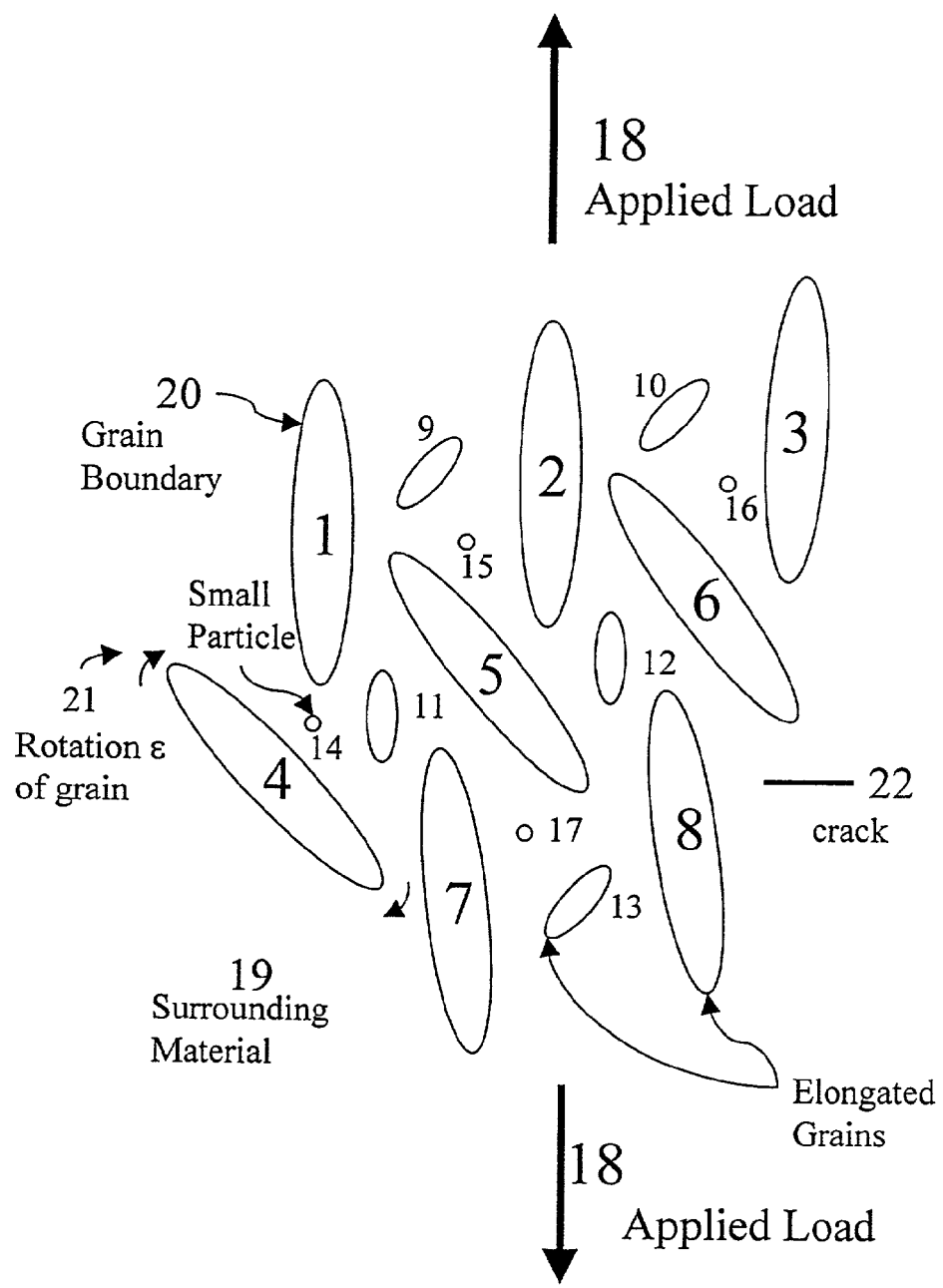
FIG. 1 is a geometrical configuration of the composite material having a microstructure model of the present invention shown with a remotely applied tensile load.

The present invention will now be described in greater detail with reference to the accompanying drawings. Referring to FIG. 1, an external or remotely applied tensile stress or load 18 is exerted upon elliptically-shaped microstructure entities or particles 1 through 17, each of which will rotate in its surrounding matrix material 19. Although microstructural entities 8 and 13 are specifically labeled as elongated grains and entity 14 as a small particle, microstructural entities 1 through 13 are similarly elongated grains and entities 14 through 17 are small particles in both FIGS. 1 and 2. As the applied load increases, an angle of rotation increases as do the induced stresses both in the matrix material and in the particles. In practice, the material discontinuity giving rise to the rotation can be a difference in the bonding and elastic properties at the particle-matrix boundary 20 itself or across the boundary.

Particles 14 to 17 may be smaller than entities 1 through 13, and may transmit compressive stresses such that their attenuation as a function of a distance r from the particle changes from a series of terms with an $r^{-n}$ dependence where n can be several integers greater than or equal to 1 to an $r^{-1}$ dependence after transmission.

The microstructural entities are grouped together in such a way that the alternating regions of tensile and compressive stresses set up from strain in the matrix from the rotation of the entities are optimized with respect to lowering the strain energy that can promote fracture. The lowering of the strain energy can come from two mechanisms. One is that the tensile and compressive stresses around and inside the microstructural entities are either themselves lower than the remote applied stress or the sum of these stresses with those concentrated stresses around cracks and cavities can be lower than the original concentrated stresses. The concentrated stress fields around cracks, pores and particles come from satisfying equilibrium and compatibility relations within the material. They have been derived theoretically by solving for stresses from stress functions when appropriate boundary conditions are used. They have also been verified experimentally through photoelasticity measurements and material testing. It is also expected that the alternating regions of tension and compression will serve as initial conditions to set up atomic lattice vibrations, whose absorption of energy will lower the strain energy available for release through the propagation of a crack.

Although shown only with entity 4, the entire group of entities 1 through 17 rotate through an angle ε21 so that the moment applied to their boundaries is zero. The moment can be written as a sum of $M_0$ and $M_{ex}$, where $M_0$ comes from the applied load and $M_{ex}$ comes from stress fields that were previously mentioned that are around cracks 22, pores in the surrounding matrix and the stress fields set up by the rotation of the microstructural entities themselves. These excess or additional forces contributing to $M_{ex}$ differ from external forces X and Y such as gravity acting on an entire body 1 through 17. They also differ from an external force possible contained in other inventions such as that on a rotating disk that causes an entire component to spin or rotate.

It is expected that the direction of rotation for each entity will depend upon the load acting locally upon it in the matrix material. While the entities that rotate may be elliptically shaped in a preferred embodiment, they may also be any other shape when a net moment occurs from the surrounding material.

Figure 2:
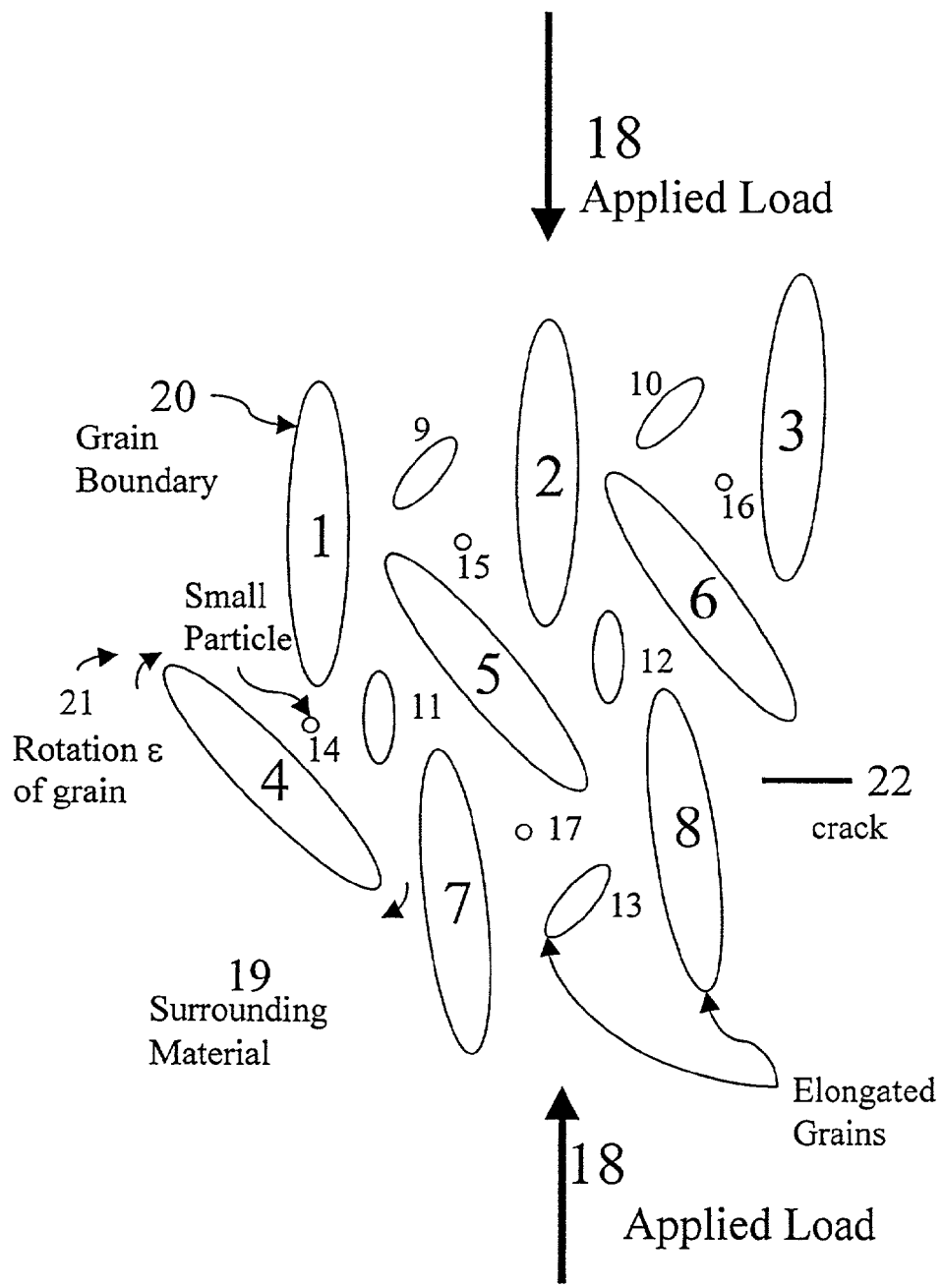
FIG. 2 is a similar view of FIG. 1, but shown with a remotely applied compressive load.

As already mentioned one source of the moment on the rotating entities may be from the applied tensile load 18 as depicted by the arrows in FIG. 1. However, this applied load may also be compressive 18 upon the composite material as shown in FIG. 2. Associated with the compressive load is an angle of rotation 21 of each microstructural entity. The direction of the rotation will also depend upon the orientation of the entity with respect to the local load on the entity so as to make the net moment zero.

Although particular embodiments of the invention have been described in detail herein with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A material model for a set of microstructural entities in a surrounding matrix material being initially in equilibrium prior to application of an applied load comprising grains, particulates and particles each being aligned at a corresponding angle with respect to the applied load such that in response to the applied load each of said entities rotates though a corresponding angle to remain in equilibrium and to create induced stresses in surrounding matrix material and in the interior of the corresponding entity that arise from strain on the matrix material resulting from the rotation of the entity.

2. The material model defined in claim 1, wherein said microstructural entities, through said rotation create alternating regions of compressive and tensile stress in both the matrix material and in the interiors of the said microstructural entities which add existing stresses around cracks, pores and particles to produce attenuated stresses and strain energy around said cracks, pores and particles.

3. The material model as defined in claim 1, wherein said particles are smaller than said grains and particulates, said smaller particles undergoing a rotation to remain in equilibrium within tensile stress fields induced by relatively larger grains by strain put on the surrounding matrix through said rotation from the applied load.

4. The material model as defined in claim 1, wherein said particles are smaller than said grains and particulates, said particles taking on one of its sides one of the induced compressive stresses from the strain in the matrix arising from the rotation of the larger grains and particulates and transmitting the compressive stress through its interior and out its other side as a point source in which the attenuation of the compressive stress changes its dependence on a function having a series of terms including $r^{-n}$ to $r^{-1}$, where r is a distance to the particles and n is r when n>1.

5. The material model as defined in claim 1, wherein said microstructural entities create through strain in the matrix and in their interiors through rotation alternating regions of tension and compression that serve as initial conditions for vibrational motion in the composite material lattice that serves to absorb strain energy whose release could promote crack propagation.

6. The material model as defined in claim 1, wherein said applied stress comprises tensile stress.

7. The material model as defined in claim 1, wherein said applied stress comprises compressive stress.

8. The material model as defined in claim 1, further including a net moment as a sum of $M_O$ from the applied load and $M_{ex}$ from the stress fields from other microstructural entities, wherein said rotational movement includes a direction of rotation, said direction being dependent upon the orientation of said microstructural entities with respect to the local applied load such that said net moment on each entity is zero.

* * * * *